(12) United States Patent
Menegazzi

(10) Patent No.: US 8,814,787 B2
(45) Date of Patent: Aug. 26, 2014

(54) ARTICULATING LARYNGOSCOPE

(75) Inventor: James John Menegazzi, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 525 days.

(21) Appl. No.: 13/262,747

(22) PCT Filed: Apr. 2, 2010

(86) PCT No.: PCT/US2010/001000
§ 371 (c)(1),
(2), (4) Date: Oct. 5, 2011

(87) PCT Pub. No.: WO2010/114621
PCT Pub. Date: Oct. 7, 2010

(65) Prior Publication Data
US 2012/0035502 A1 Feb. 9, 2012

Related U.S. Application Data

(60) Provisional application No. 61/166,037, filed on Apr. 2, 2009.

(51) Int. Cl.
*A61B 1/267* (2006.01)
*A61B 1/00* (2006.01)

(52) U.S. Cl.
CPC .............. *A61B 1/267* (2013.01); *A61B 1/00094* (2013.01); *A61B 1/0008* (2013.01)
USPC ........... 600/190; 600/191; 600/193; 600/196; 600/199

(58) Field of Classification Search
CPC .... A61B 1/267; A61B 1/0008; A61B 1/0051; A61B 1/00094

USPC .......... 600/186–188, 190, 191, 193, 196, 199
See application file for complete search history.

(56) References Cited

U.S. PATENT DOCUMENTS

| 4,592,343 A | 6/1986 | Upsher |
| 5,584,795 A | 12/1996 | Valenti |

(Continued)

FOREIGN PATENT DOCUMENTS

WO WO2007-147211 A1 12/2007

OTHER PUBLICATIONS

International Preliminary Report on Patentability for PCT Applicaiton No. PCT/US2010/001000 dated Oct. 13, 2011.

(Continued)

*Primary Examiner* — Ellen C Hammond
(74) *Attorney, Agent, or Firm* — David G. Oberdick; Peter J. Borghetti

(57) ABSTRACT

Articulating laryngoscope to aid in the intubation of patients by providing illumination of the oral cavity and trachea during the process having, for example, 'fingers' with fiber optic lights at the ends and at joints of the fingers, fingers spread open or 'flower' when the device is deployed, gently retracting and compressing soft tissues in the oral cavity and providing medical professionals with much better illumination of the passageway they are addressing, constructed from a malleable material, including rubber, plastics/polymers, and carbon fiber, instead of hard metal. The fingers may have multiple light sources to ensure a flooding of the patient's oropharynx with light. Some versions might have fiber-optic cameras connected to one or more fingers for use in teaching and research, and one might have suction capability to facilitate removal of solids and fluids, one embodiment can have at least one finger with a scalpel at its distal end.

37 Claims, 9 Drawing Sheets

(56) References Cited

U.S. PATENT DOCUMENTS

| | | |
|---|---|---|
| 5,868,668 A | 2/1999 | Weiss |
| 6,090,040 A | 7/2000 | Metro |
| 6,095,972 A | 8/2000 | Sakamoto |
| 6,123,666 A | 9/2000 | Wrenn et al. |
| 6,602,188 B2 * | 8/2003 | Bolser ............ 600/210 |
| 6,623,425 B2 | 9/2003 | Cartledge et al. |
| 6,652,453 B2 | 11/2003 | Smith et al. |
| 6,749,563 B2 | 6/2004 | Stihl |
| 6,991,604 B2 | 1/2006 | Cantrell |
| 7,044,909 B2 | 5/2006 | Berci et al. |
| 7,066,881 B2 | 6/2006 | Dietzel et al. |
| 7,798,960 B2 * | 9/2010 | Jaeger ............ 600/224 |
| 2006/0074276 A1 | 4/2006 | Cantrell |
| 2007/0213594 A1 | 9/2007 | Nguyen |
| 2008/0146880 A1 | 6/2008 | Malek |

OTHER PUBLICATIONS

International Search Report and the Written Opinion of the ISA for PCT Applicaiton No. PCT/US2010/001000 dated Nov. 12, 2010.

* cited by examiner

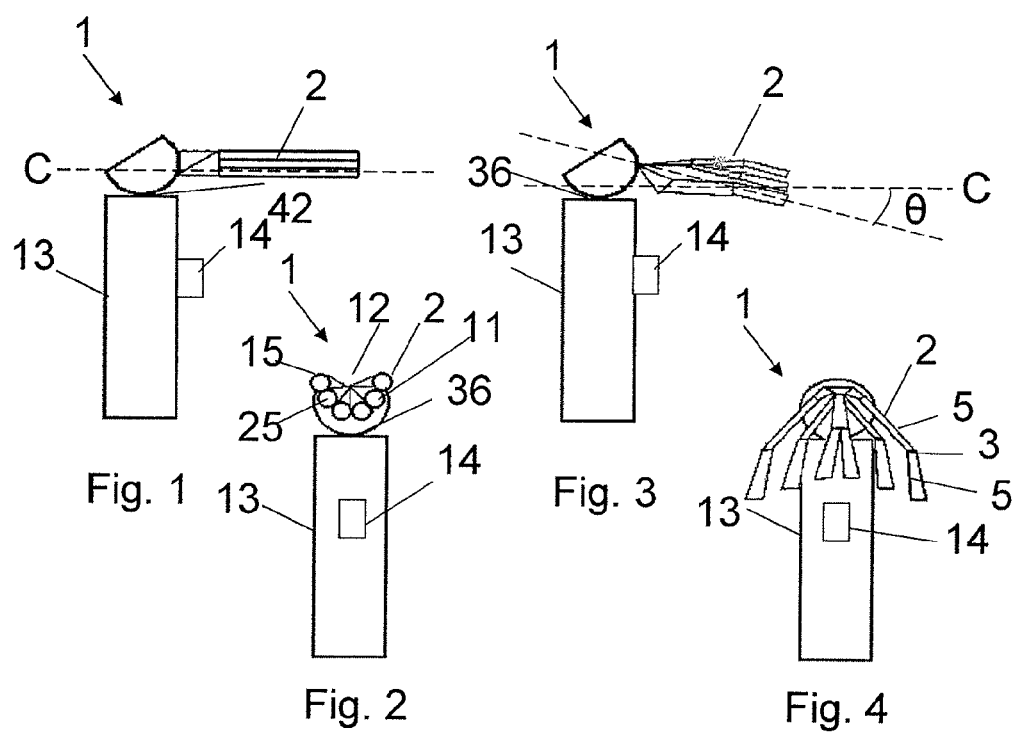

ARTICULATING LARYNGOSCOPE

CROSS REFERENCE TO RELATED APPLICATIONS

The present application is a U.S. National Stage under 35 USC 371 filing of International Application Number PCT/US2010/01000, entitled Articulating Laryngoscope filed on Apr. 2, 2010, which is a Nonprovisional Application of U.S. Provisional Application Ser. No. 61/166,037, entitled "FLOWERING LARYNGOSCOPE" filed on Apr. 2, 2009, which are both incorporated herein by reference.

FIELD OF THE INVENTION

The present invention is related generally to the field of laryngoscopes.

BACKGROUND OF THE INVENTION

The purpose of the laryngoscope is to aid in intubation. During the intubation process, a laryngoscope is used to open the airways and provide enough light to enable the user to pass an endotracheal tube through the vocal cords, securing the airway so as to provide ventilation to the lungs.

Orotracheal intubation by direct laryngoscopy is the method of airway management in critically ill and injured patients, as well as patients undergoing all types of surgery in which general anesthesia is used. Intubation is performed by anesthesiologists, nurse anesthetists, emergency medicine and critical care physicians, dentists and maxillofacial surgeons, veterinarians, and in the out-of-hospital setting by paramedics. Orotracheal intubation is performed many thousands of times daily in the US, and millions of times daily worldwide in operating rooms, emergency departments, intensive care units, and every ambulance in the world.

SUMMARY OF THE INVENTION

According to the invention, there is provided an articulating laryngoscope, as defined in claims 1-37.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which:

FIGS. 1 and 2 illustrate the side and front views, respectively, of one embodiment of articulating laryngoscope 1 of the present invention in the closed position;

FIGS. 3 and 4 illustrate the side and front views, respectively, of one embodiment of articulating laryngoscope 1 of the present invention in the deployed or open position;

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

Articulation is defined as a joint on a finger.

Actuation is defined as the movement at or about one or more joints.

Articulating laryngoscope 1 is designed to be equipped with many functional features including but not limited to, mechanical opening of air passage for ease of intubation, illumination of an air passage during intubation and for examination, delivery of gases and liquids, including medications; suction for removal of fluids including blood and mucus; cauterization to stop bleeding; removal of foreign objects and biopsy specimens; real-time video during intubation to guidance of articulating laryngoscope 1; and video recording and camera still images for evaluation and teaching; and surgical instruments including, but not limited to, scalpel, staple and suture.

Figure 5A:
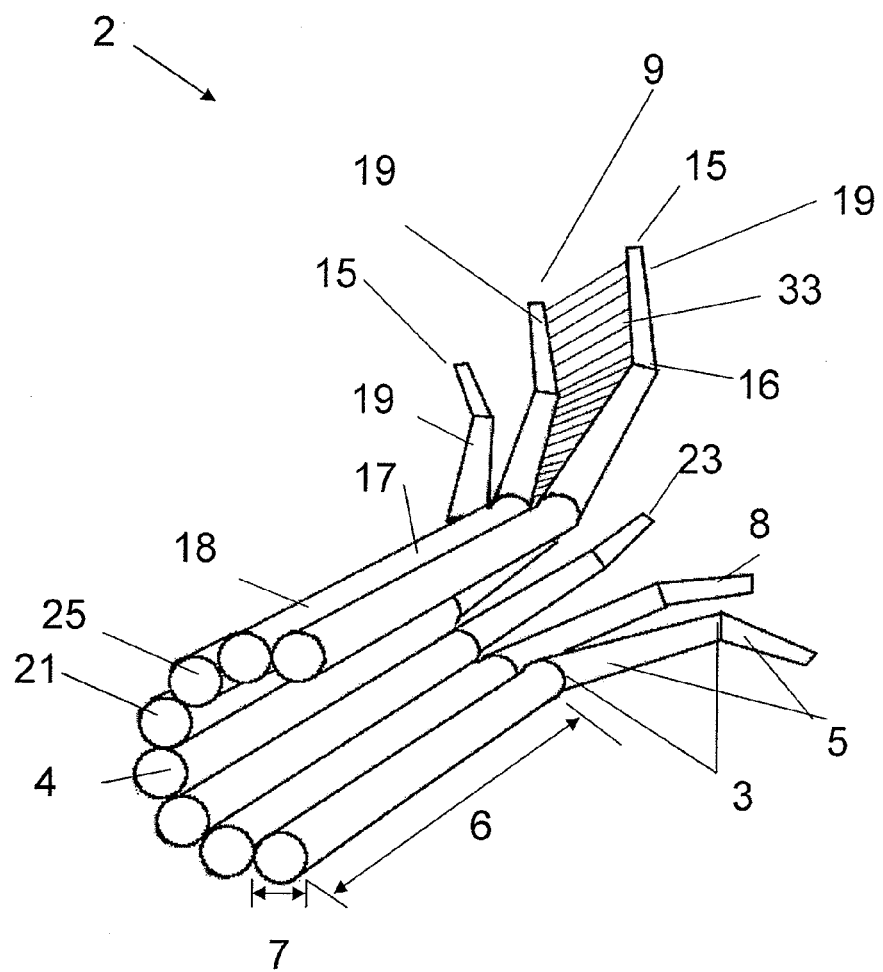
FIG. 5A is a perspective view of another embodiment of the present invention illustrating extension of the finger members.

FIGS. 1 and 2 illustrate the side and front views, respectively, of one embodiment of articulating laryngoscope 1 having six (6) fingers or projections or phalanges 2 (terms are interchangeable) arranged in a generally U or C shape configuration 11 in the closed position. The U or C shape configuration 11 provides vision for the user of the articulating laryngoscope 1 to observe the uvula, palatine tonsils, oropharynx, esophagus, larynx, and trachea as articulating laryngoscope 1 is guided into position. Therefore, open side 12 of U or C shape configuration 11 is defined as being facing up in an opposing direction relative to handle 13. Handle 13 can contain PLC 22, trigger or controller 14, AC/DC (battery) power source 29, and interfaces/ports/connections for suction source 27, oxygen source 28, and other fluid delivery input 35 (See FIG. 7). Handle 13 operably connects and communicates with fingers 2 at interface 36 by mechanical and electrical means known to one of skilled in the art FIGS. 3, 4, 5A, 5B, and 11 illustrate the structure of articulating laryngoscope 1 that provide the function of member actuation to open air passageways. Fingers 2 have joints 3 that couple together a plurality of segments 5 such that at least segments 5 of fingers 2 can articulate, which means movement upward, downward, or in a circular or elliptical path along or about a central axis C. FIG. 5A illustrates segments 5 can have different lengths 6, and thickness or diameters 7. Each segment 5 can be tapered 8 with thickness or diameter decreasing as adjacent segments 5 are attached at joints 3 from proximal end 4 and distal end 9. A plurality of segments 5 form member 19. Joints 3 provide functionality for manipulation of members 19 in many directions when actuated by a trigger 14 or other control mechanism.

Figure 5B:
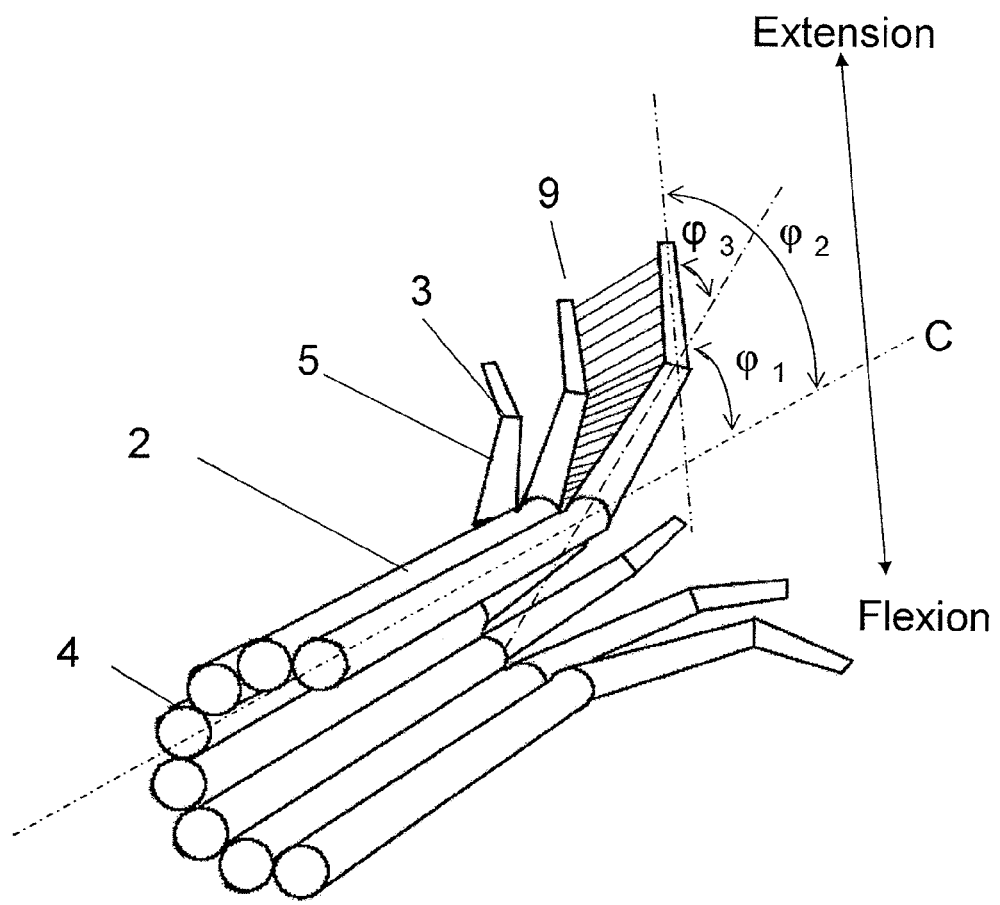
FIG. 5B is a perspective view of the embodiment of FIG. 5A illustrating relative angular positions of finger members in the extended (open) position.

FIGS. 3 and 4 illustrate side and front views, respectively, of articulating laryngoscope 1 deployed or open position where members 19 extend or flex toward, for example, tissue to open an airway of the oropharynx. FIGS. 5A-B illustrate another actuation of fingers 2 in a "flowering" arrangement where all fingers 2 are extending outwardly away from each other for the maximum opening. Fingers 2 can be manipulated to bring finger ends 15 of members 19 in contact therewith to grab or pinch an object for extraction.

Figure 6:
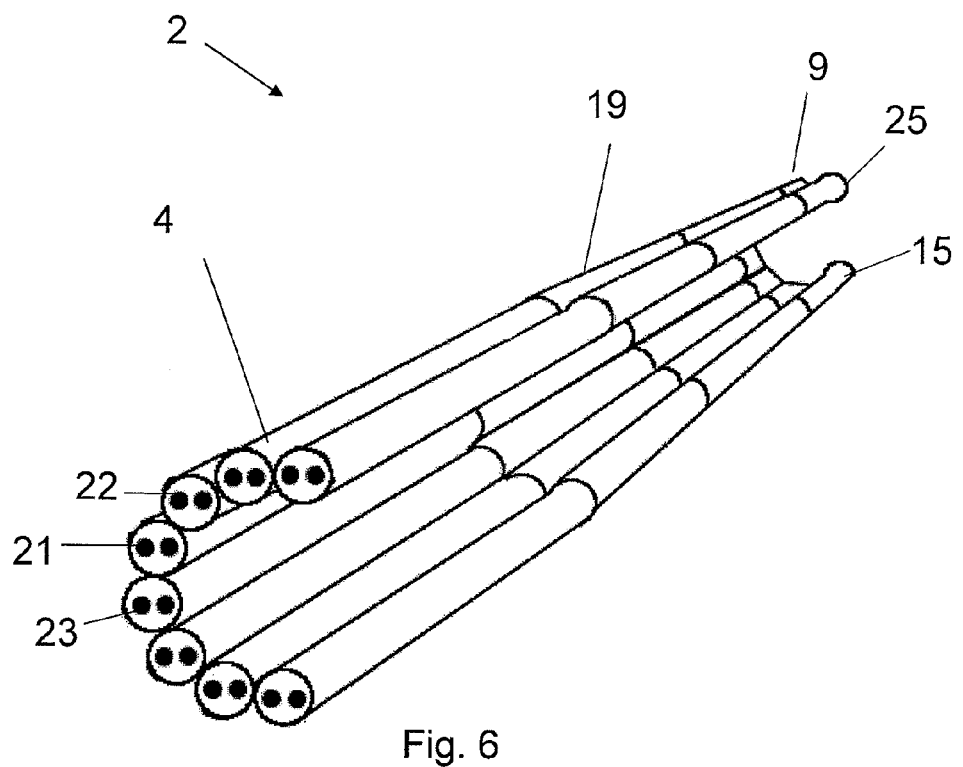
FIG. 6 is a perspective view of the embodiment in FIG. 5A in the closed position.

With regards to the actuation mechanism, FIG. 6 is an illustration of a closed laryngoscope with one or more channels that can contain embedded wires 21 for controlled finger actuation, fiber optics or light emitting diodes (LED) 22 for illumination or video, and tubes 23 for suction and fluid delivery, including oxygen and medication.

Figure 7:
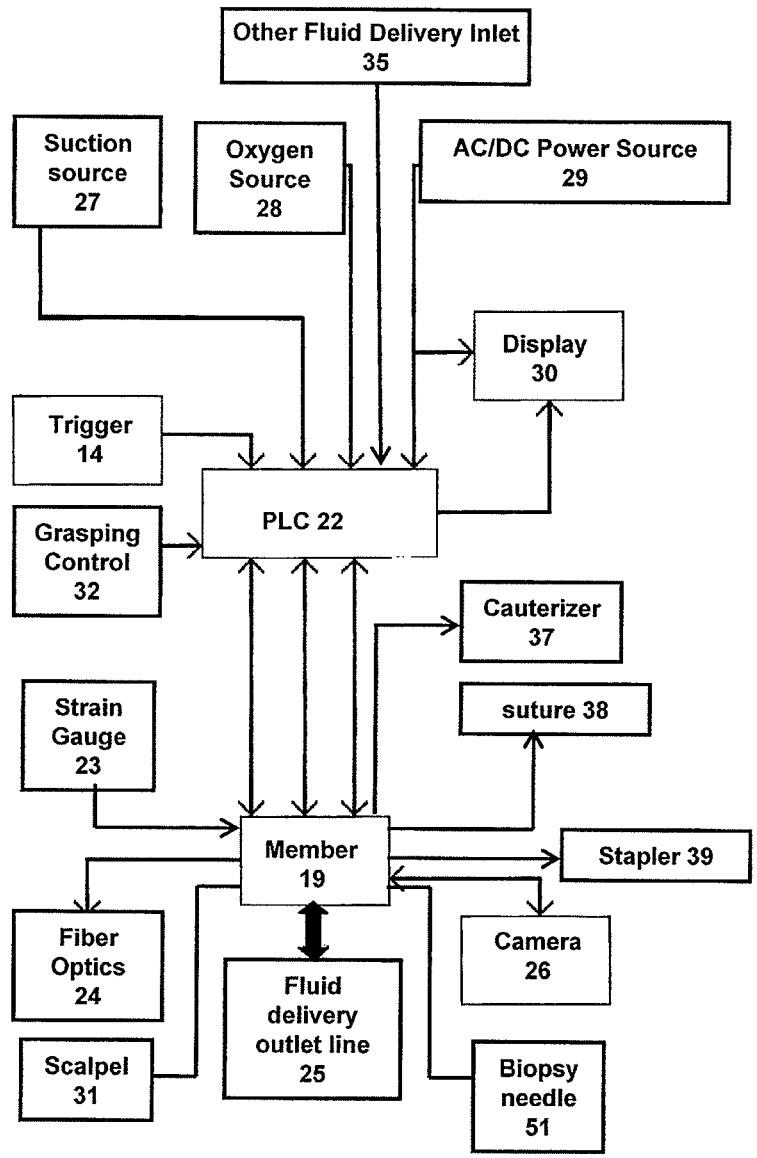
FIG. 7 is a block diagram schematic illustrating exemplary elements of the present invention.

Now turning to FIGS. 1 and 7, one embodiment of the actuation mechanism includes a handle 13 with an interface coupler 42 to operably connect handle 13 with fingers 2. Fingers 2 will interlock with handle 13 in such a way as to make physical and electrical communication with AC/DC (battery) power source 28 and PLC 22, both of which are contained in handle 13, and the moveable components in fingers 2. For instance, the actuation may be driven by manual operator energy, for example squeezing trigger 14 mechanical links to finger 2 resulting in the displacement of a physical conducting element such as a metal wire 21. At the interlocking point 36 on handle 13, wire 21 can be coupled to a flexible transducing element 40 in finger 2 or finger tip 15.

Figure 11:
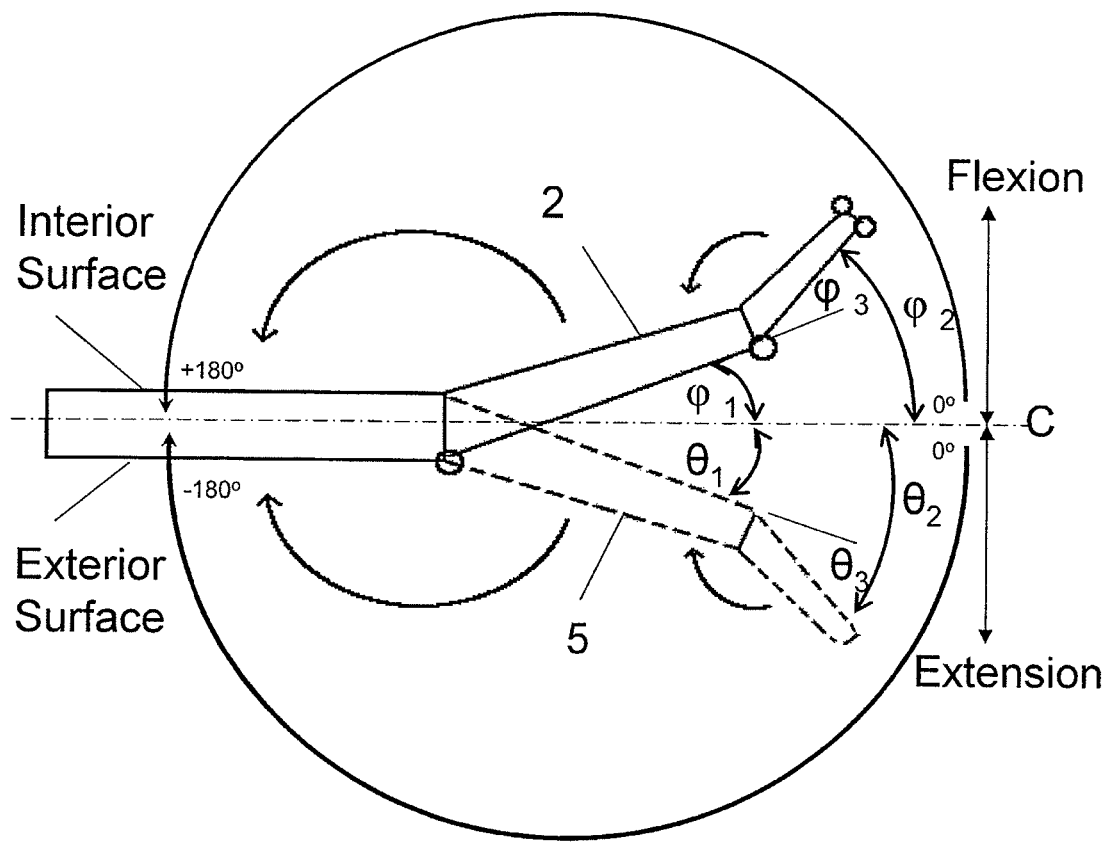
FIG. 11 is an illustration of flexion and extension of a finger member.

In one embodiment of flexible transducing element 40 can be spring hinges 41 at joints 3. Displacement of wire 21 in handle 13 will thus result in commensurate displacement of the flexible transducing element 40 in finger 2, resulting in flexion and extension of finger 2 about a central axis C (FIGS. 5B and 11). Each finger 2 has its own central axis C as illustrated in FIGS. 1, 3, 5B, and 11. Axis C can be linear or non-linear. Flexion is defined is an angular inward movement (interior surface side) $\phi_1$, $\phi_2$, $\phi_3$ (where $\phi_3=\phi_2-\phi_1$), etc. of each finger segment 5 from central axis C, about 0° up to about 180°, and any angle therebetween. Extension is defined as an angular outward movement (exterior surface side) $\theta_1$, $\theta_2$, $\theta_3$ (where $\theta_3=\theta_2-\theta_1$), etc. of each segment 5 from central axis C, about 0° up to about −180°, and any angle therebetween.

Figure 12:
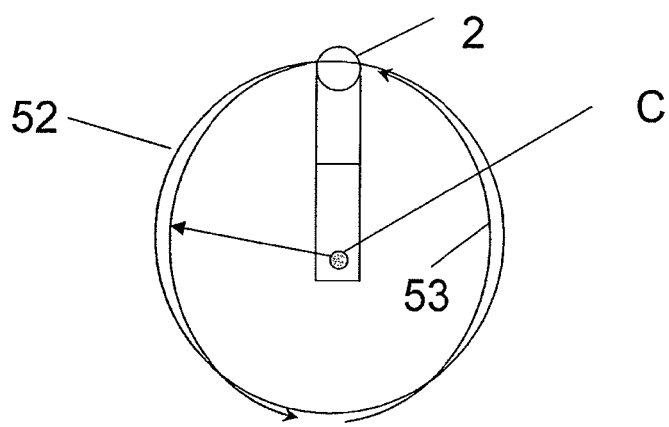
FIG. 12 is a front view of an individual finger member illustrating 360° rotational capability.

Turning now to FIG. 11 for a detailed discussion of actuation. The actuation of the individual fingers 2 can be controlled in such a way as to facilitate flexion (solid image of individual finger 2) and extension (dotted line image of individual finger 2) in two directions about a central axis C. Though the following disclosure illustrates bi-directional linear motion (up and down), it is within the contemplation of this invention that individual finger 2 can also rotate 360° about axis C (FIG. 12). The path can be circular 52 or elliptical 53 as shown in FIG. 11. This action may be accomplished by integrating two separate conducting element (such as a metal wire 21) into finger 2 and handle 13, one which transduces input energy to force for actuation, and the other which places restrictions or enables actuation in one direction about the axis while creating the opposite condition for the opposite direction. For instance, activation of the directional limiter (not shown) may slide two subsurface metal restrictors (not shown) into place and out of place, respectively, on opposite sides of a joint 5, facilitating movement toward the side without a restrictor plate, and inhibiting movement toward the side with a restrictor plate. Conduction of actuation energy will then result in movement in the former direction.

As discussed above, members 19 include an embedded actuation mechanism 20. As shown in FIG. 6, one embodiment of actuation mechanism 20 includes a pair of wires 21 extending from proximal end 4 to finger tip 15 at distal end 9. Both wires 21 are connected to trigger 14 to pull one of the wires to control actuation of a particular member 19. Another embodiment of actuation mechanism 20 can be gears (not shown) in to joints 3 linked by rotating rods connected to a motor in handle 13. Yet another embodiment of actuation mechanism 20 can be motors at joints 3 responsive to an electronic stimulus or a signal. Trigger 14 can be connected to actuation mechanism mechanically or electrically, such as by a programmable logic controller (PLC) 22 or controller with logic to determine which wire of the pair of wires to pull to actuate a member 19. One or more strain gauge 23 disposed along the length of members 19 can be used to regulate pressure of members 19 against tissue. The pressure can be monitored by the user on display 30 (FIG. 7) for manual termination of the member actuation when a pressure limit is reached or the termination can be automated with an automatic shutoff when a pressure limit is reached.

One embodiment of the present invention can lock finger 2 positions by locking of the trigger at a set displacement. Alternatively, the source of actuation may be electrical energy derived from a DC (battery) power source 29 or AC common line power source, in which case interface coupler 42 at the interface 36 on handle 13 will bring physical contact between conductive electrical wiring (not shown) in the handle and the designated in finger 2, continuing through each finger segment 5 to a successive series of motors, in series or in parallel within each finger 2.

Figure 10A:
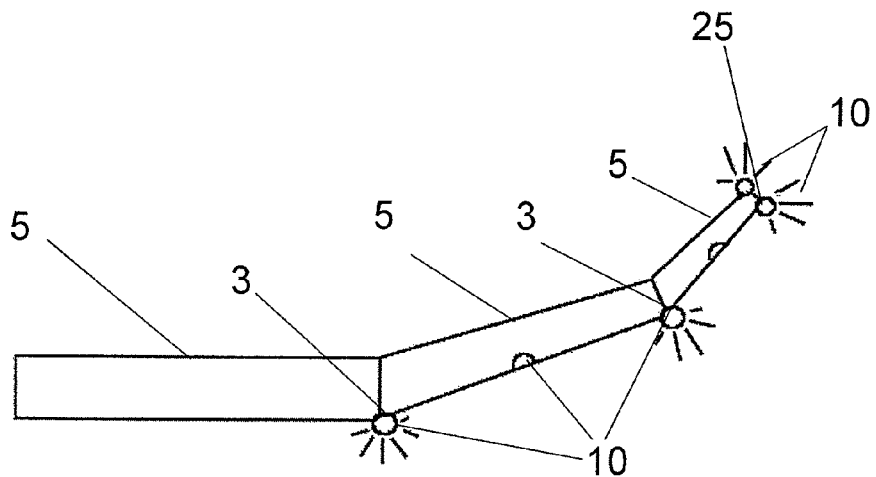
FIG. 10A-B are illustrations of the illumination system of one embodiment of the present invention.
Figure 10B:
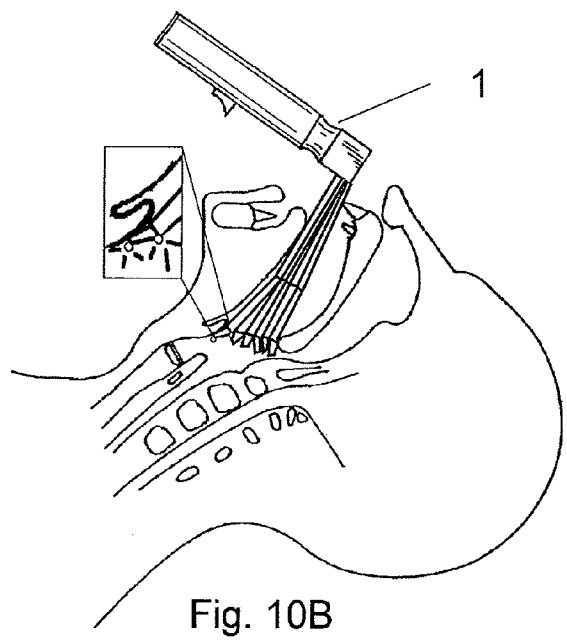

Now turning to FIGS. 10A-B illustrating one embodiment of the illumination function of the present invention. Joints 3 can include an opening 10 for light illumination when member 19 is flexed or extended or closed. FIG. 5A illustrates another embodiment for light illumination that includes finger material being made of translucent or clear substrate containing subsurface light sources 16 (fiber optics or LEDs) below the external surface 17 of the material to protect the light source 16 from contamination or prevent malfunctioning of joint 3 due to blockage caused by foreign objects. FIG. 10B illustrates illumination of the oropharynx to view the trachea and esophagus for intubation with the light illumination system of the present invention.

Joints 3 can also use opening 10 for suction or other fluid delivery when member 19 is flexed or extended (FIG. 10A) or closed. Openings 10 can be disposed along segments 5 in any location, such as midway between joints 3. Finger 2 can include a fluid delivery outlet 25 at finger end 15 capable of delivering forced air or other medical gases (including oxygen), liquids and medicines (FIG. 2) as well as suction. A balloon (not shown) can be fluidly connected to end 15 of finger 2 by fluid delivery line 25 for inflation to open up the passage way or to close off a passage way.

Now returning to FIG. 5A illustrate another embodiment of the present invention including webbing 33 between members 19 to function as a barrier to hold back tissues such as the tongue, fluids (such as blood, saliva, mucus), food particles, or other foreign objects that obscure the vision of the user and block the passageway. Webbing 33 can be disposed between one pair of member 19 (as shown in FIG. 5A) or between all members 19.

FIG. 7 illustrates exemplary functions and component connectivity of articulating laryngoscope 1. PLC 22 can control illumination of lights on/off/brightness/direction adjustment; suction on/off/pressure; automatic member actuation shutdown when members 19 exceeds a range of motion limit or when a strain gauge 23 embedded in finger tip 15 exceeds pressure limit; optical focus and field of view; camera on/off/video/still images/run time shutoff/routing of optical signal to display 30/lens directional adjustment; scalpel actuation measured by depth of cut into tissue and stroke length of cut;

oxygen flow rate and mixture; suction flow rate; grasping control logic 32 that accounts for strain gauge 23 readings to adjust actuation of members 19 to assure grasping pressure is not beyond crush limits to avoid destruction or disintegration of object within the patient.

Other embodiments of articulating laryngoscope 1 can also include the following features:

A. grasping control 32 can include member 19 pinching function to stop, for example, bleeding;

B. member 19 can include an endotracheal tube mounted on it;

C. member 19 can include a cauterizer mounted on end 15 to stop bleeding;

D. member 19 can be constructed in multiple sizes for infants, toddlers, teenager, adults, and animals. Size can also be adapted for dental use, vaginal examinations and procedures, and other cavity examinations and procedures.

E. member 19 can include a biopsy needle 51.

Fingers 2 can be a monolithic structure formed from a single injection mold. Finger base structure 18 can be rigid at proximal end 4 over segment length 6, where there is no relative movement between members 19. The remaining portion of members 19 can be independently operable and moveable relative to adjacent members 19.

Another embodiment of fingers 2 can be a plurality of assembled components wherein a plurality of members 19 are mechanically connected at joints 3 by any conventional means such as ball and socket, hinges, or straps. Materials for fingers 2 and members 19 can include plastic, carbon fiber, polymers, any semi-rigid material, or combination thereof. Material can have antibiotic and healing properties. Members 19 are sufficiently malleable to be self contouring to tissue during actuation that will distribute the force or pressure substantially evenly to prevent point contact for a prolonged period to minimize tissue damage.

Materials for handle 13 can include stainless steel, aluminum, plastic, carbon fiber, rubber, polymers, any semi-rigid material, or combination thereof.

Figure 8A:
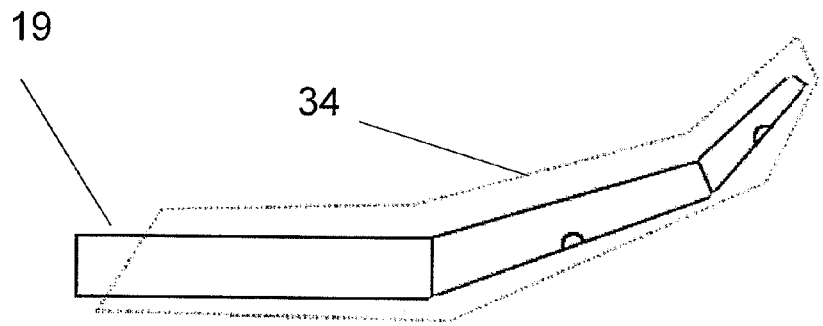
FIGS. 8A-C are illustrations of a protective sleeve.
Figure 8B:
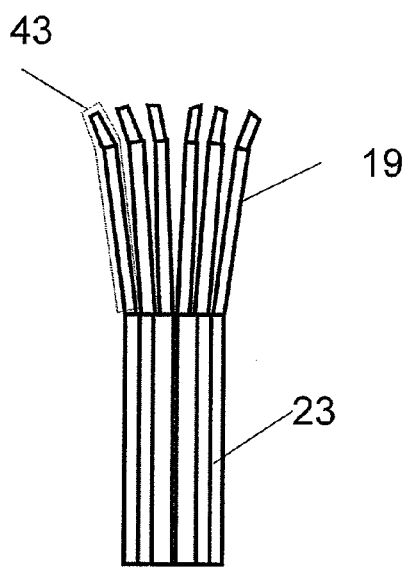
Figure 8C:
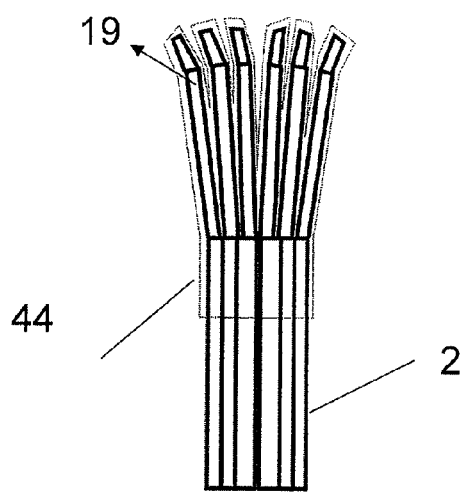

Now turning to FIGS. 8A-C, disposable sleeve 34 can be slipped over member 19 without webbing to function as a protective covering for reusable fingers 2 to either minimize or eliminate the need for sterilization. One embodiment of sleeve 43 can be used for a single member 19 (FIG. 8B). Another embodiment of sleeve 44 can be used for an entire finger 2 assembly (FIG. 8C) similar to a glove.

Figure 9A:
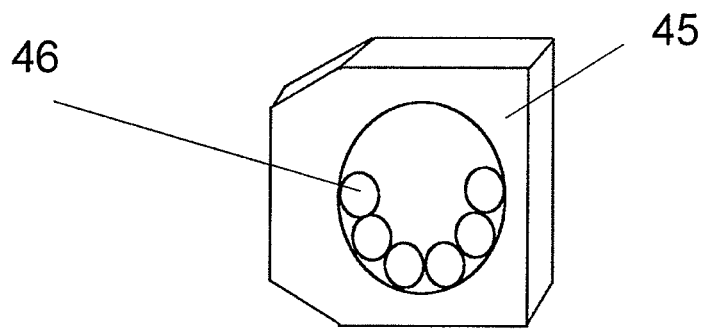
FIGS. 9A-C are illustrations of modular finger holder embodiments.
Figure 9B:
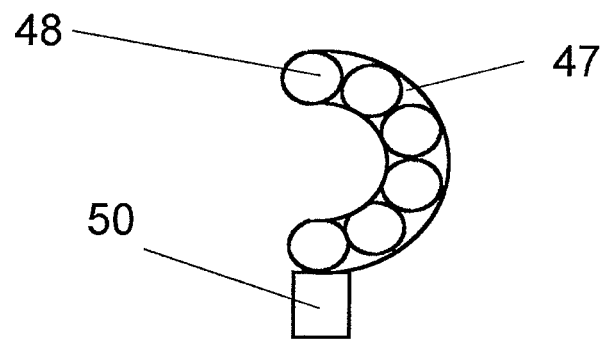
Figure 9C:
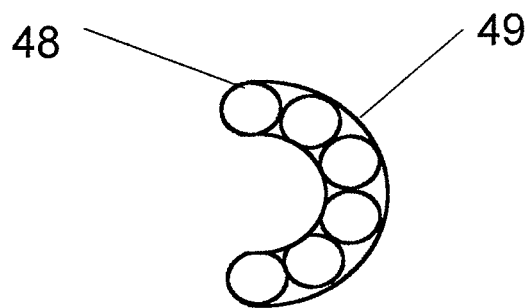

Another embodiment of the present invention is modular and includes separate, removable fingers 2 that can be selected for its function (such as suction, fluid delivery, light optics, camera lens, and scalpel) and fitted within a holder for a plurality of fingers 2. Fingers 2 can be made of a low cost, sterile material for disposable purposes or the fingers can be made of materials designed for repeated use and sterilization between uses. Now turning to FIGS. 9A-C with illustrations of embodiments of the present invention with a finger base for modular configurations to hold individual members 2. FIG. 9A illustrates one embodiment of block holder 45 made of malleable material (for example plastic) for individual finger 2. Block holder 45 includes finger attachment devices 46 that can be a hole to receive individual member 2 therein, or a pin to receive individual member 2 thereon. Pin 46 can include a hole therethrough for suction or fluid delivery. Block 45 can directly connect with handle 13. FIGS. 9B-C illustrate holder embodiments 47, 49 being generally U or C shaped and made of malleable material (for example plastic) having hole 48 to receive individual member 2 therein. Holder 47 includes a block 50 that can used to secure holder 47 while inserting and removing individual fingers 2. Individual fingers 2 inserted into holder 47, 49 can directly connect to handle 13.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A laryngoscope comprising;
   a handle having a trigger mechanism; and
   a plurality of members,
      wherein the plurality of members are arranged to form a U or C shaped configure having an open end opposingly oriented to the handle,
      wherein each member of the plurality of members has a central axis C when the laryngoscope is in a closed position,
      wherein the member of each plurality of members is operably connected to the trigger mechanism, wherein actuation of the trigger mechanism can selectively extend each member above the central axis C and flex each member below the central axis C.

2. The laryngoscope according to claim 1, wherein each member of the plurality of members has a different central axis C than an adjacent member.

3. The laryngoscope according to claim 1, wherein each member of the plurality of members comprises a plurality of segments, wherein each segment of the plurality of segments is coupled longitudinally to an adjacent segment.

4. The laryngoscope according to claim 1, wherein the plurality of members are monolithic.

5. The laryngoscope according to claim 1, wherein the plurality of members are independent members capable of being disposed in a holder to form the plurality of members.

6. The laryngoscope according to claim 5, wherein the holder has a U or C shaped configuration.

7. The laryngoscope according to claim 1, wherein each member comprises a tip, wherein the tips of two members can be articulated toward each other such that the tips of the two members contact each other for grasping an object.

8. The laryngoscope according to claim 7, wherein the tip comprises a strain gauge in communication with a programmable logic controlled to determine pressure limit exceedance.

9. The laryngoscope according to claim 8, wherein the programmable logic controller is connected to a display device.

10. The laryngoscope according to claim 8, wherein the programmable logic controller monitors a strain gauge and terminates actuation of at least one member when a strain measurement exceeds a predetermined level.

11. The laryngoscope according to claim 1, wherein actuation of the trigger selectively extends outward one or more members to contact and push outward tissue to open a passage.

12. The laryngoscope according to claim 1, wherein actuation of the trigger selectively flexes inward one or more members.

13. The laryngoscope according to claim 1, further comprises webbing between two members.

14. The laryngoscope according to claim 1, wherein each member is adapted to comprise a light source.

15. The laryngoscope according to claim 14 wherein the light source is disposed at a tip of each member.

16. The laryngoscope according to claim 14 wherein the light source is disposed between joints of each member.

17. The laryngoscope according to claim 14 wherein the light source is disposed below a surface of each member.

18. The laryngoscope according to claim 17 wherein the surface is an internal surface of each member.

19. The laryngoscope according to claim 17 wherein the surface is an external surface of each member.

20. The laryngoscope according to claim 1, wherein each member is adapted to comprise a fluid delivery tube.

21. The laryngoscope according to claim 1, wherein each member is adapted to comprise a suction tube.

22. The laryngoscope according to claim 21 further comprising a suction port fluidly connected to the suction tube being disposed at a tip of each member.

23. The laryngoscope according to claim 21 further comprising a suction port fluidly connected to the suction tube being disposed between joints of each member.

24. The laryngoscope according to claim 1, wherein each member is adapted to comprise a scalpel.

25. The laryngoscope according to claim 1, wherein each member is adapted to comprise a stapler.

26. The laryngoscope according to claim 1, wherein each member is adapted to comprise a cauterizer.

27. The laryngoscope according to claim 1, wherein each member is adapted to comprise a camera.

28. The laryngoscope according to claim 1, wherein each member is adapted to comprise a strain gauge.

29. The laryngoscope according to claim 1, wherein the handle comprises a programmable logic controller in communication with each member.

30. The laryngoscope according to claim 1, wherein each member is adapted to comprise a biopsy needle.

31. The laryngoscope according to claim 1, further comprising a protective sleeve capable of being disposed over each member.

32. The laryngoscope according to claim 1, wherein actuation of the trigger selectively actuates one or more members in a circular motion.

33. The laryngoscope according to claim 1, wherein each member is adapted to comprise a suture.

34. The laryngoscope according to claim 1, further comprising a power source or a power source adapter in the handle being operably connected to the plurality of members.

35. The laryngoscope according to claim 1, wherein each member is adapted to comprise a fiber optic cable.

36. The laryngoscope according to claim 14 wherein the light source is disposed at a joint of each member.

37. The laryngoscope according to claim 1 wherein the handle further comprises at least one inlet port for a suction source, oxygen source, or other fluid delivery.

\* \* \* \* \*

UNITED STATES PATENT AND TRADEMARK OFFICE
CERTIFICATE OF CORRECTION

PATENT NO. : 8,814,787 B2
APPLICATION NO. : 13/262747
DATED : August 26, 2014
INVENTOR(S) : David D. Salcido Page 1 of 1

It is certified that error appears in the above-identified patent and that said Letters Patent is hereby corrected as shown below:

On the Title Page, Item (12) delete "Menegazzi" and insert --Salcido--.
On the Title Page, Item (75) Inventor should read
--(75) Inventor: David D. Salcido, Pittsburgh, PA (US)--

Signed and Sealed this
Twenty-third Day of June, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,814,787 B2 | |
| APPLICATION NO. | : 13/262747 | |
| DATED | : August 26, 2014 | |
| INVENTOR(S) | : Menegazzi et al. | |

It is certified that error appears in the above-identified patent and that said Letters Patent is hereby corrected as shown below:

Title Page, Item (12) "Menegazzi" should read -- Menegazzi, et al. --.
Title Page, Item (75) Inventor is corrected to read:
-- James John Menegazzi, Pittsburgh (PA);
   David D. Salcido, Pittsburgh, (PA) --.

This certificate supersedes the Certificate of Correction issued June 23, 2015.

Signed and Sealed this
Twenty-ninth Day of March, 2016

Michelle K. Lee
*Director of the United States Patent and Trademark Office*